United States Patent [19]

Bourgery et al.

[11] 4,113,951
[45] Sep. 12, 1978

[54] AMINOALKOXYBENZOFURANS

[75] Inventors: Guy R. Bourgery, Colombes; Alain P. Lacour, La Varenne; Bernard M. Pourrias, Meudon la Foret; Geneviève C. Bregeon, Paris, all of France

[73] Assignee: Delalande S. A., Courbevoie, France

[21] Appl. No.: 813,357

[22] Filed: Jul. 6, 1977

[30] Foreign Application Priority Data

Jul. 12, 1976 [FR] France .................................. 76 21287
Jun. 27, 1977 [FR] France .................................. 77 19658

[51] Int. Cl.² ................... C07D 405/12; C07D 405/14
[52] U.S. Cl. ............................... 544/360; 260/293.58; 260/295 E; 260/326.36; 260/346.73; 424/250; 424/267; 424/274; 424/285; 544/376
[58] Field of Search ............... 260/268 BC, 293.58, 260/346.73, 326.36, 295 E

[56] References Cited

U.S. PATENT DOCUMENTS 3,850,937  11/1974  Fauran et al. ................... 260/293.58

Primary Examiner—Paul M. Coughlan, Jr.
Attorney, Agent, or Firm—Blanchard, Flynn, Thiel, Boutell & Tanis

[57] ABSTRACT

Aminoalkoxybenzofurans having the formula

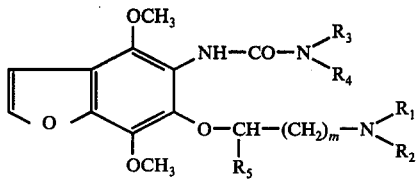

wherein

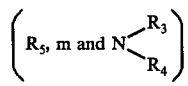

are either (1)

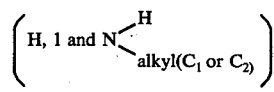

and

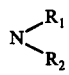

is monoalkylamino, dialkylamino, cycloalkylamino or heterocyclic amino, or (2)

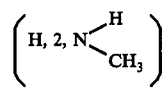

(H, 1, 4-methyl piperazino),

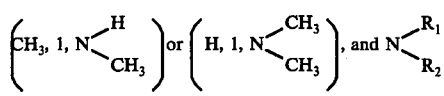

is piperidino. The compounds possess antidysrhythmic properties.

13 Claims, No Drawings

AMINOALKOXYBENZOFURANS

The present invention has as its aim aminoalkoxybenzofurans, the method of their preparation and their application in therapeutics. These compounds correspond more precisely to the formula:

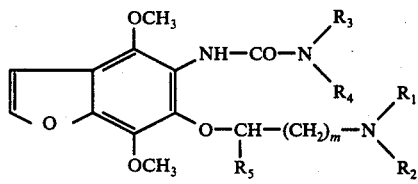
(I)

in which the whole of the three parameters

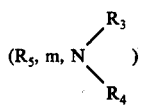

takes on any one of the following values:

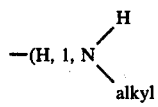

where the alkyl group comprises 1 or 2 carbon atoms) in which case

represents a monoalkylamino group in which the alkyl group comprises 1 to 3 carbon atoms, a dialkylamino group in which the alkyl groups comprise 1 to 3 carbon atoms, a cycloalkylamino group comprising 5 or 6 carbon atoms or a heterocyclic radical, particularly pyrrolidino, piperidino, hexamethyleneimino, heptamethyleneimino, 4-methyl piperidino, 4-methyl piperazino and 1,2,5,6-tetrahydro pyridino; and

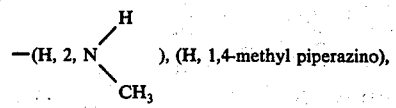

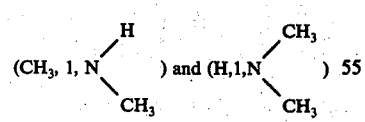

in which cases

represents a piperidino radical.

The method of the invention consists:
(a) in treating 5-acetamino 4,7-dimethoxy 6-hydroxy benzofuran of formula:

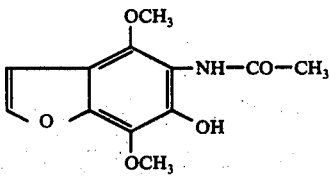
(II)

described in French Pat. No. 2,178,815, with a dilute hydrochloric acid solution to obtain the compound:

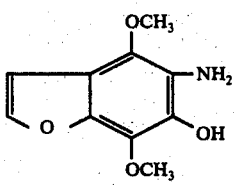
(III)

also described in French Pat. No. 2,178,815 which is condensed:
on isocyanates of formula:

R'$_4$NCO         (IV)

in which R'$_4$ represents a methyl or ethyl group, in chloroform at room temperature, or
on dimethylcarbamoyl chloride of formula:

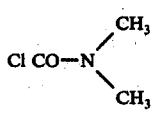
(V)

to reflux in chloroform or in toluene in an autoclave, to obtain compounds of formula:

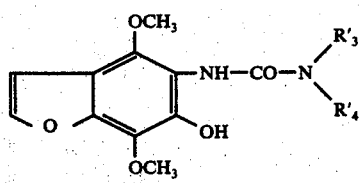
(VI)

in which the group

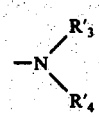

represents a methylamino, ethylamino or dimethylamino group, then in condensing the compounds of formula (VI):
either with chlorated amines of formula:

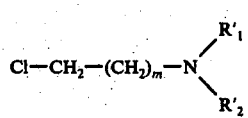
(VII)

in which

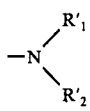

represents a dialkylamino group in which the alkyl groups comprise from 1 to 3 carbon atoms, or a heterocyclic radical, particularly pyrrolidino, piperidino, hexamethyleneimino, heptamethyleneimino, 4-methyl piperidino, 4-methyl piperazino and 1,2,5,6-tetrahydro pyridino; and $m$ being equal to 1 or 2, to reflux in acetone or in acetonitrile in the presence of potassium carbonate, which leads to compounds of formula:

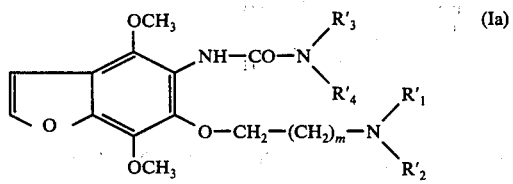

in which the groups

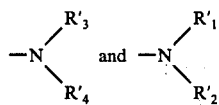

have the same significance as in
formulae (VI) and (VII) respectively, $m$ being equal to 1 or 2;
or with halogenated derivatives of formula:

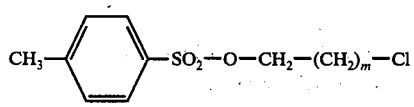

in which $m$ has the value 1 or 2 at 90° C. in 50% aqueous soda, or halogenated derivatives of formulae:

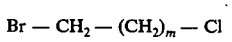

or

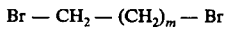

in which $m$ has the value of 1 or 2, to reflux in acetone or acetonitrile in the presence of potassium carbonate; and in reacting on the new compounds thus obtained of formula:

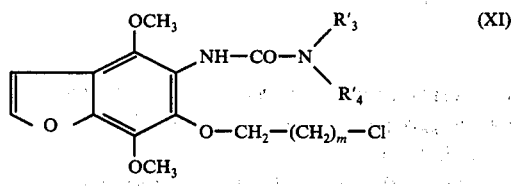

in which $m$ has the value 1 or 2, and the group

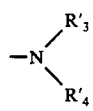

has the same significance as in formula (VI), amines of formula:

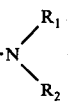

in which the group

has the same significance as in formula (VII) and may moreover represent a monoalkylamino group in which the alkyl group comprises 1 to 3 carbon atoms and a cycloalkylamino group comprising 5 to 6 carbon atoms, in toluene in an autoclave at a temperature of 100° to 110° C. which leads to compounds of formula:

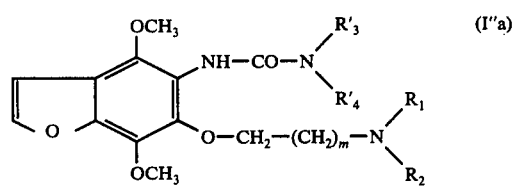

or, when

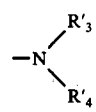

in formula (VI) represents a monomethylamino group, with chlorated amide of formula:

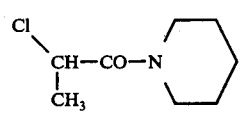

to reflux in acetone or acetonitrile in the presence of potassium carbonate to obtain the compound of formula:

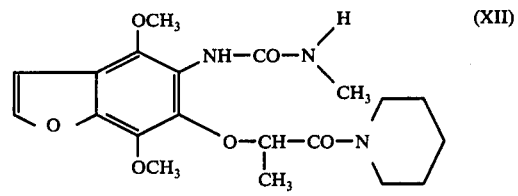

which is then reduced with the lithium and aluminium hydride, to reflux in tetrahydrofuran, which leads to the compound of formula:

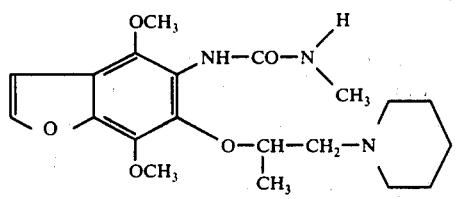
(Ib)

(b) or by reacting the compound of said formula (II) with a chlorated amine of formula:

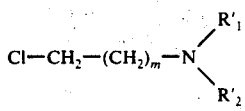
(VII)

to reflux in acetone or acetonitrile in the presence of potassium carbonate, or with any one of the halogenated derivatives of formulae:

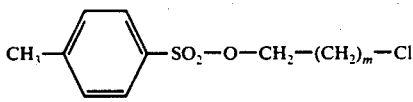
(VIII)

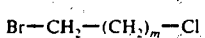 (IX)

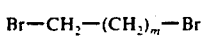 (X)

in which $m$ is equal to 1 or 2, in 50% aqueous soda in the case of the derivative of formula (VIII) and in acetone or acetonitrile in the presence of potassium carbonate in the other cases, and in condensing the compounds thus obtained of formula:

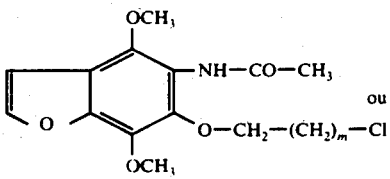
(XV)

ou with amines of formula:

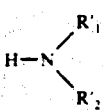
(XVI)

in which

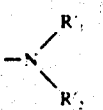

has the same significance as in formula (VII) in toluene in an autoclave, which leads to obtaining compounds of formula:

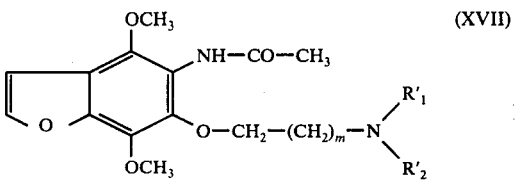
(XVII)

in which $m$ is equal to 1 or 2 and

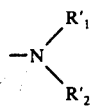

has the same significance as in formula (XVI), which is treated with a diluted hydrochloric acid solution to obtain compounds of formula:

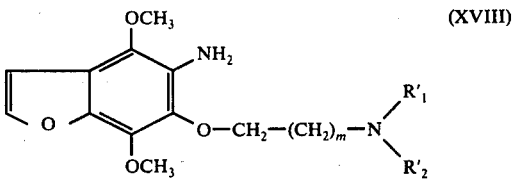
(XVIII)

where $m$ and

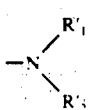

have the same significance as in formula (XVII), which are reacted:

with said isocyanates of formula (IV), in toluene in an autoclave to obtain compounds of formula:

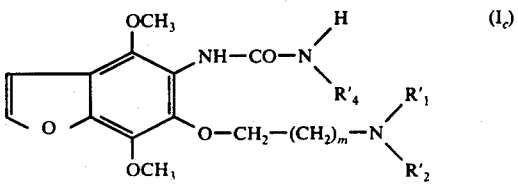
(I$_c$)

in which $R'_4$ has the same significance as in formula (IV) and

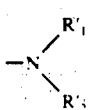

has the same significance as in formula (XVIII), and $m$ is equal to 1 or 2, or, when

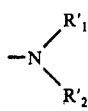

represents a piperidino radical and m is equal to 1 or 2, with said dimethyl carbamoyl chloride of formula (V), to obtain the compound of formula:

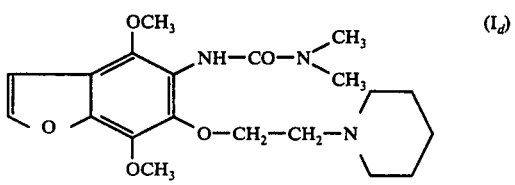

this reaction being carried out in toluene at room temperature.

The compound of formula:

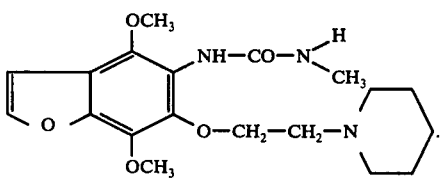

prepared in accordance with the above method may then be reacted with N-methylpiperazine of formula:

to reflux in toluene which leads to the compound of formula:

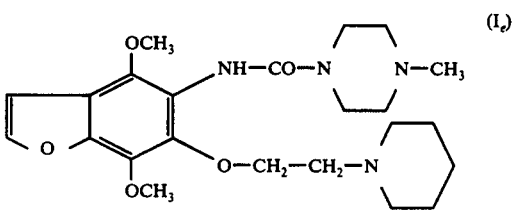

The following preparations are given solely as examples to illustrate the invention.

EXAMPLE 1: 4,7-Dimethoxy 6-(2-isopropylamino ethoxy), 5-N-methyl carbamoyl amino benzofuran. Code number: 770 576

First Step: 4,7-dimethoxy 5-N-methylcarbamoyl amino 6-hydroxy benzofuran. Code number: 760 945

To a solution of 20.9 g (0.1 mole) of 5-amino 4,7-dimethoxy 6-hydroxy benzofuran in 200 ml of chloroform was slowly added 5.7 g (0.1 mole) of methyl isocyanate. It was stirred at room temperature for 2 hours, then the solvent was evaporated and the residue was crystallized in ether and filtered. 23 g of the desired product were obtained.
Yield: 89%
Melting point: 110° C.
Empirical formula: $C_{12}H_{14}N_2O_5$

| Elementary analysis: | C | H | N |
| --- | --- | --- | --- |
| Calculated (%) | 54.13 | 5.30 | 10.52 |
| Obtained (%) | 54.03 | 5.36 | 10.48 |

Second step: 6-(2-chloro ethoxy) 4,7-dimethoxy 5-N-methylcarbamoyl amino benzofuran. Code number: 770 653

A mixture of 150 g (0.56 mole) of the compound obtained in the preceding step, 100 ml (1.2 mole) of 2-chloro 1-bromo ethane and 207 g (1.5 mole) of potassium carbonate was brought to reflux for 4½ hours in 1.4 l of acetonitrile.

It was filtered hot, cooled and the precipitate formed was filtered. 115 g of the desired product was obtained.
Yield: 62%
Melting point: 148° C.
Empirical formula: $C_{14}H_{17}Cl\ N_2O_5$

| Elementary analysis | C | H | N |
| --- | --- | --- | --- |
| Calculated (%) | 57.53 | 5.52 | 9.50 |
| Obtained (%) | 57.46 | 5.49 | 9.48 |

Third step: 4,7-dimethoxy 6-(2-isopropylamino ethoxy) 5-N-methylcarbomoyl amino benzofuran. Code number: 770 576

A solution of 11.5 g (0.035 mole) of 6-(2-chloro ethoxy) 4,7-dimethoxy 5-N-methylcarbamoyl amino benzofuran obtained in the preceding step, 8.2 g (0.14 mole) of isopropylamine, 7.5 g (0.05 mole) of sodium iodide and 4.8 g (0.035 mole) of potassium carbonate in 200 ml of toluene was brought to reflux in an autoclave for 15 hours. It was filtered; the filtrate was evaporated and recrystallized in ethyl acetate. 2.2 g of the desired product were obtained.
Yield: 18%
Melting point: 140° C.
Empirical formula: $C_{17}H_{25}N_3O_5$

| Elementary analysis: | C | H | N |
| --- | --- | --- | --- |
| Calculated (%) | 58.10 | 7.17 | 11.96 |
| Obtained (%) | 57.89 | 7.11 | 11.86 |

EXAMPLE 2: 6-(2-diisopropylamino ethoxy) 4,7-dimethoxy 5-N-methylcarbamoyl amino benzofuran. Code number: 770 266

A suspension of 12 g (0.045 mole) of 4,7 dimethoxy 5-N-methylcarbamoyl amino 6-hydroxy benzofuran obtained in the first step of example 1, 12 g (0.06 mole) of 2-diisopropylamino 1-chloro ethane hydrochloride and 21 g (0.15 Mole) of potassium carbonate in 100 ml of acetonitrile were brought to reflux for 4 hours. It was filtered, the filtrate was evaporated and the residue recrystallized in a 50/50 mixture of ethyl acetate and isopropylic ether. Thus were obtained 13.5 g of the desired product.
Yield: 77%
Melting point: 142° C.
Empirical formula: $C_{20}H_{31}N_3O_5$

| Elementary analysis: | C | H | N |
|---|---|---|---|
| Calculated (%) | 61.05 | 7.94 | 10.68 |
| Obtained (%) | 61.22 | 7.94 | 10.62 |

EXAMPLE 3: 4,7-dimethoxy-5-(4-methyl piperazinocarbamoylamino) 6-(2-piperidino ethoxy) benzofuran. Code number: 770 520

First step: 5-amino 4,7-dimethoxy 6-piperidinoethoxy benzofuran dichlorhydrate. Code number: 740 778

A solution of 25.1 g (0.1 mole) of 5-acetamido 4,7-dimethoxy 6-piperidinoethoxy benzofuran were brought to reflux for 10 hours in 200 ml of 2 N hydrochloric acid. Then it was neutralized with concentrated soda, extracted with ethyl acetate, the solvent was evaporated, the residue was taken up again in acetone and 30 ml of 7 N hydrochloric ethanol were added. It was filtered and recrystallized in ethanol.

Melting point: 203° C.
Yield: 43%
Empirical formula: $C_{17}H_{26}Cl_2N_2O_4$

| Elementary analysis: | C | H | N |
|---|---|---|---|
| Calculated (%) | 51.48 | 6.74 | 6.91 |
| Obtained (%) | 51.72 | 6.63 | 6.81 |

Second step: 4,7-dimethoxy 5-N-methylcarbamoylamino-6-(2-piperidino ethoxy) benzofuran. Code number: 750 819

A mixture of 16 g (0.05 mole) of 5-amino 4,7-dimethoxy 6-piperidinoethoxy benzofuran prepared in the preceding step and 3.2 ml (0.055 mole) of methyl isocyanate were brought to 80°–90° C. for 3 hours, in an autoclave, in 500 ml of toluene. The solvent was evaporated, the oil obtained was crystallized in petroleum ether and recrystallized in isopropylic ether.

Melting point: 120° C.
Yield: 37%
Empirical formula: $C_{19}H_{27}N_3O_5$

| Elementary analysis | C | H | N |
|---|---|---|---|
| Calculated (%) | 60.46 | 7.21 | 11.13 |
| Obtained (%) | 60.42 | 7.29 | 11.30 |

Third step: 4,7-dimethoxy 5-(4-methyl piperazinocarbamoyl amino) 6-(2-piperidino ethoxy) benzofuran. Code number: 770 520

A solution of 8.5 g (0.023 mole) of 4,7-dimethoxy 5-N-methylcarbamoyl amino 6-12-piperidino ethoxy) benzofuran obtained in the preceding step and 9.1 g (0.09 mole) of N-methylpiperazine in 100 ml of toluene was brought to reflux for 20 hours. The solvent was evaporated, the residue taken up again in ethyl acetate and washed with water, the solvent was evaporated, the residue was crystallized in ether and recrystallized in ethyl acetate.

Yield: 25%
Melting point: 138° C.
Empirical formula: $C_{23}H_{34}N_4O_5$

| Elementary analysis | C | H | N |
|---|---|---|---|
| Calculated (%) | 61.86 | 7.68 | 12.55 |
| Obtained (%) | 61.63 | 7.70 | 12.33 |

EXAMPLE 4: 4,7-dimethoxy 5-N-methylcarbamoyl amino 6-(2-piperidino 1-methyl ethoxy) benzofuran. Code number: 770 422

First step: 4,7-dimethoxy 5-N-methylcarbamoyl amino 6-(1-piperidinocarbonyl ethoxy) benzofuran.

A suspension of 13.3 g (0.05 mole) of 4,7-dimethoxy 5-N-methylcarbamoyl amino 6-hydroxy benzofuran obtained in the first step of example 1, 12 g (0.068 mole) of 1-chloro 1-piperidinocarbonyl ethane and 13.8 g (0.1 mole) of potassium carbonate in 120 ml of acetonitrile was brought to reflux for 6 hours. Then it was filtered, the filtrate evaporated, the residue taken up again in chloroform and filtered on a silica column. 8.5 g (0.02 mole) of the desired compound were obtained, i.e. a yield of 41%.

Second Step: 4,7-dimethoxy 5-N-methylcarbamoylamino 6-(2-piperidino 1-methyl ethoxy) benzofuran.

The compound obtained in the preceding step was dissolved in 50 ml of tetrahydrofuran and the solution obtained was slowly added to a suspension of 2.3 g of lithium and aluminium hydride in 100 ml of tetrahydrofuran. It was brought to reflux for 4 hours, then hydrolized and filtered, the filtrate was evaporated and the residue chromatographed on a silica column.

By elution with chloroform, 5 g of the expected product were obtained which was recrystallized in the 20% ethyl acetate-80% isopropylic ether mixture.

Yield: 50%
Melting point: 147° C.
Empirical formula: $C_{20}H_{29}N_3O_5$

| Elementary analysis: | C | H | N |
|---|---|---|---|
| Calculated (%) | 61.36 | 7.47 | 10.74 |
| Obtained (%) | 61.15 | 7.73 | 10.58 |

EXAMPLE 5: 4,7-dimethoxy 5-N-methylcarbamoylamino 6-(2-piperidino ethoxy) benzofuran. Code number: 750 819

First step: 5-acetamido 4,7-dimethoxy 6-(2-piperidino ethoxy) benzofuran hydrochlorate. Code number: 740 745

A mixture of 25.1 g (0.1 mole) of 5-acetamido 4,7-dimethoxy 6-hydroxy benzofuran, 22.2 g (0.15 mole) of 2-piperidino chlorethane and 41.6 g (0.3 mole) of potassium carbonate in 250 ml of acetone was brought to reflux for 2 hours. Then it was filtered, the solvent evaporated, the residue obtained was taken up again in acetone and 20 ml of 7 N hydrochloric ethanol were added. It was filtered and recrystallized in 400 ml of propanol.

Melting point: 260° C.
Yield: 33%
Empirical formula: $C_{19}H_{27}Cl\ N_2O_5$

| Elementary analysis: | C | H | N |
|---|---|---|---|
| Calculated (%) | 57.21 | 6.82 | 7.02 |
| Obtained (%) | 57.35 | 7.03 | 7.08 |

Second step: 5-amino 4,7-dimethoxy 6-(2-piperidino ethoxy) benzofuran dichlorhydrate. Code number: 740 778

A solution of 25.1 g (0.1 mole) of 5-acetamido 4,7-dimethoxy-(2-piperidino ethoxy) benzofuran prepared in the previous step, in 200 ml of 2 N hydrochloric acid, was brought to reflux for 10 hours. Then it was neutralized with concentrated soda, extracted with ethyl acetate, the solvent was evaporated, the residue was taken up again in acetone and 30 ml of 7 N hydrochloric ethanol were added. It was filtered and recrystallized in ethanol.

Melting point: 203° C.
Yield: 43%
Empirical formula: $C_{17}H_{26}Cl_2N_2O_4$

| Elementary analysis: | C | H | N |
|---|---|---|---|
| Calculated (%) | 51.48 | 6.74 | 6.91 |
| Obtained (%) | 51.72 | 6.63 | 6.81 |

Third step: 4,7-dimethoxy 5-N-methylcarbamoylamino 6-(2-piperidino ethoxy) benzofuran. Code number: 750 819

A mixture of 16 g (0.05 mole) of 5-amino 4,7-dimethoxy 6-(2-piperidino ethoxy) benzofuran prepared in the preceding step and 3.2 ml (0.055 mole) of methyl isocyanate was brought to 80°-90° C. for 3 hours, in an autoclave, in 500 ml of toluene. Then the solvent was evaporated, the oil obtained was crystallized in petroleum ether and recrystallized in propylic ethanol.

Melting point: 120° C.
Yield: 37%
Empirical formula: $C_{19}H_{27}N_3O_5$

| Elementary analysis: | C | H | N |
|---|---|---|---|
| Calculated (%) | 60.46 | 7.21 | 11.13 |
| Obtained (%) | 60.42 | 7.29 | 11.30 |

EXAMPLE 6: 5-acetamido-6-(2-chloro ethoxy) 4,7-dimethoxy benzofuran. Code number: 750 885

A solution of 25.1 g (0.1 mole) of 5-acetamido 4,7-dimethoxy 6-hydroxy benzofuran in 15 ml of a 50% aqueous solution of soda was brought to 90° C. and 21 g (0.1 mole) of 2-chloro ethanol tosylate was slowly added, it was ketp at 90° C. for 2 hours, diluted in 1 l of water, filtered and recrystallized in ethanol.

Yield: 37%
Melting point: 180° C.
Empirical formula: $C_{14}H_{16}Cl N O_5$

| Elementary analysis: | C | H | N |
|---|---|---|---|
| Calculated (%) | 53.59 | 5.14 | 4.46 |
| Obtained (%) | 53.41 | 5.21 | 4.75 |

EXAMPLE 7: 5-acetamido 4,7-dimethoxy 6-(4-methyl piperazino ethoxy) benzofuran hydrated dichlorhydrate. Code number: 750 934

A solution of 15.5 g (0.05 mole) of 5-acetamido 6-(2-chloro ethoxy) 4,7 dimethoxy benzofuran prepared in the preceding example and 15 g (0.15 mole) of N-methyl piperazine was brought to reflux for 8 hours in 100 ml of toluene. It was filtered and the filtrate evaporated under vacuum the residue was taken up again in alcohol and hydrochloric alcohol was added. It was filtered and recrystallized in absolute alcohol.

Yield: 55%
Melting point: 160° C.
Empirical formula: $C_{19}H_{29}Cl_2N_3O_5 + 9/4\ H_2O$

| Elementary analysis: | C | H | N |
|---|---|---|---|
| Calculated (%) | 46.48 | 6.88 | 8.56 |
| Obtained (%) | 46.76 | 6.73 | 8.34 |

It should be noted that with the process of the second step of example 1, but using the corresponding reagents, 6-(3-chloro propoxy) 4,7 dimethoxy 5-N-methylcarbamoyl-amino benzofuran was obtained, code No. 770 564, having the following characteristics:

Melting point: 162° C.
Empirical formula: $C_{15}H_{19}Cl\ N_2O_5$
RMN spectrum (δ ppm - DMSO):
7.92 and 7.03, d, (J = 3 Hz)-2 benzofurannic protons,
7.11, s, 1 urea proton:

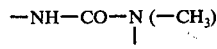

5.98, d, (J = 5 Hz), 1 urea proton: —N—CO—NH (—CH₃)
3.85 and 3.96, s, 6 protons (2 CH₃O—)
centered on 3.92, m, 4 protons,

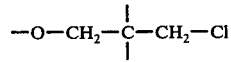

centered on 2.10, m, 2 protons,

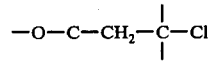

2.63, d, (J = 5 Hz), 3 protons

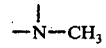

With the process of the third step of example 1, but using the corresponding reagents, the compounds of code numbers 770 602, 770 577 and 770 578 are obtained, they are shown in Table 1 below.

With the process of example 2 using the corresponding reagents the compound of code 750 819 is obtained.

Likewise, with the process of the first step of example 5 and using the corresponding reagents, the compounds are obtained of code numbers 750 725, 750 761, 750 762, 760 886, 760 887, 750 732 and 770 191 shown in table II below.

With the process of the second step of example 5 and using the corresponding reagents the compounds of formula (XVIII) are obtained for which:

$m$ has the value 1 and

represents a dimethylamino, diethylamino, pyrrolidino, hexamethyleneimino or heptamethyleneimino group, and $m$ has the value 2 and

represents the piperidino radical, as well as the compound of code number 760 618 for which $m$ has the value 1 and

represents the 4-methyl piperazino group having the following characteristics:
Melting point: 62° C.
Yield ≃ 100%
Empirical formula: $C_{17}H_{25}N_3O_4$

| Elementary analysis: | C | H | N |
|---|---|---|---|
| Calculated (%) | 60.87 | 7.51 | 12.53 |
| Obtained (%) | 60.56 | 7.62 | 12.67 |

TABLE I

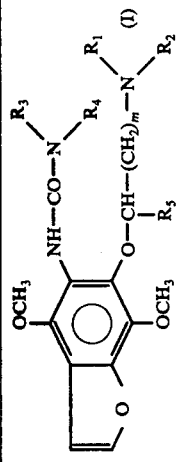

| Code No. | -N(R1)(R2) | -N(R3)(R4) | R5 | m | Empirical formula | Molecular weight | Melting point (°C) | Yield (%) | Calculated (%) C | Calculated (%) H | Calculated (%) N | Obtained (%) C | Obtained (%) H | Obtained (%) N |
|---|---|---|---|---|---|---|---|---|---|---|---|---|---|---|
| 760 677 | piperidine | —NH—Et | H | 1 | $C_{20}H_{29}N_3O_5$ | 391.46 | 112 | 83 | 61.36 | 7.47 | 10.74 | 61.29 | 7.63 | 11.11 |
| 770 206 | N(CH3)2 | " | " | " | $C_{16}H_{23}N_3O_5$ | 337.37 | 143 | 53 | 56.96 | 6.87 | 12.46 | 56.74 | 6.59 | 12.43 |
| 770 193 | N(Et)2 | —NH—CH3 | " | " | $C_{18}H_{27}N_3O_5$ | 365.42 | 134 | 58 | 59.16 | 7.45 | 11.50 | 59.05 | 7.43 | 11.68 |
| 770 266 | N(C3H7 iso)2 | " | " | " | $C_{20}H_{31}N_3O_5$ | 393.47 | 142 | 77 | 61.05 | 7.94 | 10.68 | 7.94 | 10.62 | |
| 770 207 | pyrrolidine | " | " | " | $C_{18}H_{25}N_3O_5$ | 363.40 | 116 | 37 | 59.49 | 6.93 | 11.56 | 59.17 | 677 | 11.53 |
| 760 954 | piperidine | " | " | " | $C_{20}H_{29}N_3O_5$ | 390.45 | 130 | 61 | 61.36 | 7.47 | 10.74 | 61.43 | 7.38 | 10.77 |
| 760 989 | azepane | " | " | " | $C_{21}H_{31}N_3O_5$ | 405.48 | 122 | 64 | 62.20 | 7.71 | 10.36 | 61.90 | 7.51 | 10.44 |
| 770 422 | piperidine | " | CH3 | " | $C_{20}H_{29}N_3O_5$ | 391.46 | 147 | 50 | 61.36 | 7.47 | 10.74 | 61.15 | 7.73 | 10.58 |
| 760 955 | " | " | H | 2 | $C_{20}H_{29}N_3O_5$ | 391.46 | 137 | 59 | " | " | " | 61.21 | 7.60 | 10.60 |
| 760 722 | N-methylpiperazine | " | H | 1 | $C_{19}H_{28}N_4O_5 + H_2O$ | 410.46 | 118 | 80 | 55.59 | 7.37 | 13.65 | 55.48 | 7.08 | 13.93 |

TABLE I-continued

| Code No. | -N(R₃)(R₄) | -N(R₁)(R₂) | R₅ | m | Empirical formula | Molecular weight | Melting point (°C) | Yield (%) | Calculated (%) C | Calculated (%) H | Calculated (%) N | Obtained (%) C | Obtained (%) H | Obtained (%) N |
|---|---|---|---|---|---|---|---|---|---|---|---|---|---|---|
| 770 201 | | 4-methylcyclohexyl-N | " | " | C₂₀H₂₉N₃O₅ | 391.46 | 133 | 75 | 61.36 | 7.47 | 10.74 | 61.04 | 7.34 | 10.89 |
| 770 336 | -N(CH₃)-NH-CH₃ | 2-methylpiperidinyl | " | " | " | 391.46 | 114 | 50 | " | " | " | 61.41 | 7.43 | 10.58 |
| 770 602 | " | -NH-C₃H₇-iso | " | " | C₁₅H₂₁N₃O₅ + ½H₂O | 336.85 | 147 | 62 | 53.48 | 6.73 | 12.48 | 53.72 | 6.35 | 12.45 |
| 770 576 | " | cyclohexyl-NH | " | " | C₁₇H₂₅N₃O₅ | 351.39 | 140 | 48 | 58.10 | 7.17 | 11.96 | 57.89 | 7.11 | 11.86 |
| 770 577 | " | cyclohexyl-NH | " | " | C₂₀H₂₉N₃O₅ | 391.46 | 135 | 60 | 61.36 | 7.47 | 10.74 | 61.18 | 7.41 | 10.43 |
| 770 578 | " | tetrahydropyridinyl-N | " | " | C₁₉H₂₅N₃O₅ | 375.41 | 128 | 78 | 60.78 | 6.71 | 11.19 | 60.66 | 6.68 | 10.99 |
| 770 520 | 4-methylpiperazinyl-N | piperidinyl-N | " | " | C₂₃H₃₄N₄O₅ | 446.53 | 138 | 35 | 61.86 | 7.68 | 12.55 | 61.63 | 7.70 | 12.33 |
| 750 819 | -NH-CH₃ | piperidinyl-N | " | " | C₁₉H₂₇N₃O₅ | 377.43 | 120 | 37 | 60.46 | 7.21 | 11.13 | 60.42 | 7.29 | 11.30 |

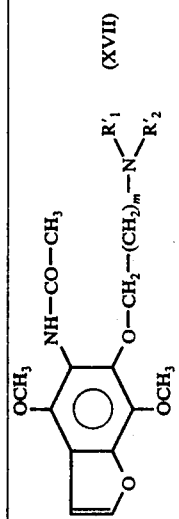

| $-N\begin{matrix}R'_1\\R'_2\end{matrix}$ | Code No. | Form | m | Empirical formula | Molecular weight | Melting point (° C) | Yield (%) | Calculated (%) C | Calculated (%) H | Calculated (%) N | Obtained (%) C | Obtained (%) H | Obtained (%) N |
|---|---|---|---|---|---|---|---|---|---|---|---|---|---|
| piperidine | 740 745 | chlorohydrate | 1 | $C_{19}H_{27}ClN_2O_5$ | 398.88 | 260 | 33 | 57.21 | 6.82 | 7.02 | 57.35 | 7.03 | 7.08 |
| azocane-CH₃/CH₃ | 750 725 | methane sulfonate | " | $C_{19}H_{28}N_2O_8S$ | 444.49 | 148 | 60 | 51.34 | 6.35 | 6.30 | 51.42 | 6.38 | 6.37 |
| -N(Et)(Et) | 750 761 | chlorohydrate + H₂O | " | $C_{16}H_{23}ClN_2O_6$ | 376.83 | 110 | 40 | 50.99 | 6.69 | 7.43 | 51.13 | 6.61 | 6.97 |
| -N(Et)(Et) | 750 762 | methane sulfonate + H₂O | " | $C_{19}H_{32}N_2O_9S$ | 464.53 | 85 | 42 | 49.12 | 6.94 | 6.03 | 48.87 | 6.94 | 5.82 |
| piperidine | 750 732 | methane sulfonate | 2 | $C_{21}H_{35}N_2O_8S$ | 472.55 | 188 | 65 | 53.37 | 6.83 | 5.93 | 53.36 | 7.13 | 5.74 |
| azocane | 760 886 | chlorohydrate | 1 | $C_{20}H_{29}ClN_2O_5$ | 412.90 | 218 | 80 | 58.17 | 7.08 | 6.79 | 58.06 | 7.12 | 6.87 |
| azocane | 760 887 | " | " | $C_{21}H_{31}ClN_2O_5$ | 426.93 | 189 | 67 | 59.08 | 7.32 | 6.56 | 58.92 | 7.47 | 6.57 |
| 4-methylpiperidine | 770 191 | chlorohydrate + 3/5 H₂O | " | $C_{20}H_{28}N_2O_5$ + 3/5 H₂O | 423.71 | 170 | 79 | 56.69 | 7.18 | 6.61 | 56.45 | 7.24 | 6.34 |
| N-methylpiperazine | 750 934 | dichlorohydrate + 9/4 H₂O | " | $C_{19}H_{27}N_3O_5$ + 9/4 H₂O | 490.90 | 160 | 55 | 46.48 | 6.88 | 8.56 | 46.76 | 6.73 | 8.34 |

The compounds of formula (I) of the invention have been studied on laboratory animals and showed antidysrhythmic properties.

Two tests brought out these properties.

First test

The compounds of formula (I) inhibit for more than 30 minutes a ventricular tachycardia inducted by an overdose of ouabain in a dog anaesthetized with sodic pentobarbitol (30 mg/kg./i.v;)

The results obtained with several of them, as well as the results obtained with reference substances (ajmaline, quinidine, procainamide, diisopyramide and amiodarone) well known for their antidysrhythmic activity are shown in Table III below.

It is to be noted that the tested compounds are injected intravenously 30 minutes after establishment of the stability of the ventricular tachycardia.

TABLE III

| Compound tested | Ventricular tachycardia induced in a dog by ouabain | |
|---|---|---|
| | Dose re-establishing the sinusal rhythm (mg/kg/i.v.) | Duration of effect (min.) |
| According to the invention : | | |
| 750 819 | 2.4 | 9 to 105 |
| 760 677 | 2 | 90 to 120 |
| 770 206 | 4 | >120 |
| 770 193 | 2 | 120 |
| 770 266 | 2 | 30 to 120 |
| 770 207 | 2 | 60 |
| 760 954 | 1 | 120 |
| 760 989 | 2 | <30 |
| 770 422 | 1 | <20 |
| 760 955 | 2 | 105 |
| 760 722 | 5 | 120 |
| 770 201 | 2 | 15 to 30 |
| 770 336 | 2 | 30 |
| 770 602 | 2 | 30 |
| 770 576 | 4 | 120 |
| 770 577 | 0.5 | 10 |
| 770 578 | 4 | 15 to 120 |
| 770 520 | 1 | 120 |
| Reference : | | |
| QUINIDINE | 8.8 | 30 |
| PROCAINAMIDE | 30 | 30 |
| AJAMALINE | 2.5 | 30 |
| DIISOPYRAMIDE | 5 | 30 |
| AMIODARONE | inactive to 9 | |

Second Test

The compounds of formula (I) permit the sinusal rhythm to be reestablished in a wakeful dog with polymorphous ventricular dysrhythmia 24 hours after the ligature of the anterior interventricular artery according to the technique of Harris.

The results obtained with several of them, as well as the results obtained with reference substances (ajmaline, quinidine, procainamide, diisopyramide, amiodarone) well known for their antidysrhythmic activity, are given in Table IV below, the compounds listed being administered by slow intravenous injection of by mouth by forced feeding.

TABLE IV

| Compounds tested | Polymorphous dysrhythmia induced in a dog by ligature of a coronary artery | | | |
|---|---|---|---|---|
| | Dose administered (mg/kg/i.v.) | % re-establishment of the sinusal rhythm | Dose administered (mg/kg/p.o.) | % re-establishment of the sinusal rhythm |
| According to the invention | | | | |
| 750 819 | 5 | 100 | 12.5 | 90 |
| 760 677 | 2 | 90 | | |
| 770 206 | | | | |
| 770 193 | | | | |
| 770266 | 2 | 30 | | |
| 770 207 | 2 | 60 | | |
| 760 954 | 2 | 50 | 12.5 | 80 |
| 760 989 | 2 | 100 | | |
| 770 422 | | | | |
| 760 955 | 2 | 80 (½) of animals) | | |
| 760 722 | 5 | 50 | | |
| 770 336 | 2 | 30 | | |
| Reference | | | | |
| QUINIDINE | 10 | 42 | 25 | 25 |
| PROCAINAMIDE | 5 | 35 | <60 | Inactive |
| AJMALINE | 2.5 | 25 | 35 | |
| DIISOPYRAMIDE | 5 | 45 | 125 | 55 |
| AMIODARONE | 10 | 42 (48 hours) | 50 | Inactive |

As is clear from the results shown in Tables III and IV and from those appearing in Table V below, the difference between the pharmacologically active doses and the lethal doses is sufficiently large to allow the compounds of formula (I) to be used in therapeutics.

TABLE V

| Compounds tested | 50 lethal dose (mouse) (mg/kg/i.v.) |
|---|---|
| According to the invention | |
| 760 677 | 28 |
| 770 206 | 100 |
| 770 193 | 74 |
| 770 266 | 52 |
| 770 207 | 98 |
| 760 954 | 31 |
| 760 988 | 14 |
| 770 422 | 30 |
| 760 955 | 42.5 |
| 760 722 | 145 |
| 770 201 | 24 |
| 770 336 | 25 |
| 770 602 | 67 |
| 770 576 | 49 |
| 770 577 | 9.5 |
| 770 578 | 72 |
| 770 520 | 16 |
| 750 819 | 56 |
| Reference | |
| QUINIDINE | 89 |
| PROCAINAMIDE | 140 |
| AJMALINE | 26 |
| DIISOPYRAMIDE | 60 |
| AMIODARONE | 150 |

It should be noted moreover that most of the compounds of formula (I) have an antidysrhythmic activity equal to or greater than that of the reference compounds.

The compounds of formula (I) are indicated in disorders of the cardiac rhythm, as for example tachycardia.

They will be administered orally in the form of tablets, pills, capsules, containing from 1 to 200 mg of active ingredient (2 to 6 per day) or parenterally in the form of injectable ampoules containing from 1 to 100 mg of active ingredient (1 to 4 per day).

What we claim is:

1. A compound having the formula

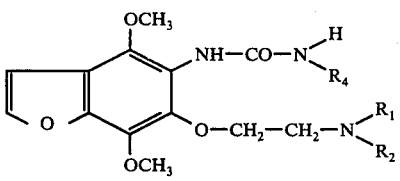

wherein R₄ is methyl or ethyl, and

is pyrrolidino, piperidino, hexamethyleneimino, heptamethyleneimino, 4-methyl piperidino, 4-methyl piperazino, or 1,2,5,6-tetrahydropyridino.

2. A compound according to claim 1 wherein R₄ is ethyl and

is piperidino.

3. A compound according to claim 1 wherein R₄ is methyl and

is pyrrolidino.

4. A compound according to claim 1 wherein R₄ is methyl and

is hexamethyleneimino.

5. A compound according to claim 5 wherein R₄ is methyl and

is heptamethyleneimino.

6. A compound according to claim 1 wherein R₄ is methyl and

is piperidino.

7. A compound according to claim 1 wherein R₄ is methyl and

is 4-methyl piperidino.

8. A compound according to claim 1 wherein R₄ is methyl and

is 4-methyl piperazino.

9. A compound according to claim 1 wherein R₄ is methyl and

is 1,2,5,6-tetrahydropyridino.

10. A compound having the formula

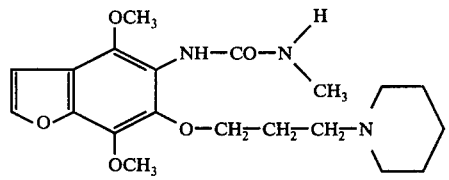

11. A compound having the formula

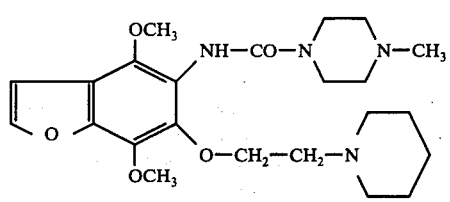

12. A compound having the formula

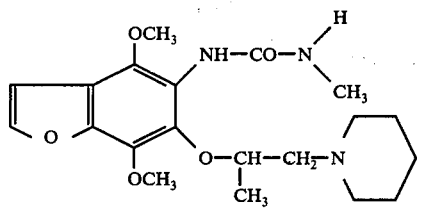

13. A compound having the formula

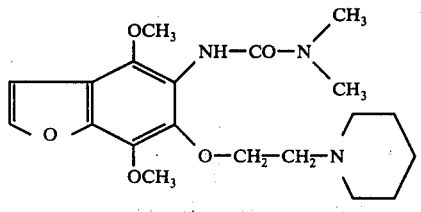

* * * * *

UNITED STATES PATENT AND TRADEMARK OFFICE
CERTIFICATE OF CORRECTION

PATENT NO. : 4 113 951
DATED : September 12, 1978
INVENTOR(S) : Guy R. Bourgery et al It is certified that error appears in the above-identified patent and that said Letters Patent are hereby corrected as shown below:

Column 23, line 54; change "5" to ---1---.

Signed and Sealed this

Twenty-sixth Day of December 1978

[SEAL]

Attest:

RUTH C. MASON
*Attesting Officer*

DONALD W. BANNER
*Commissioner of Patents and Trademarks*